United States Patent [19]

Vary et al.

[11] Patent Number: 4,851,331

[45] Date of Patent: Jul. 25, 1989

[54] METHOD AND KIT FOR POLYNUCLEOTIDE ASSAY INCLUDING PRIMER-DEPENDANT DNA POLYMERASE

[75] Inventors: Calvin P. H. Vary, Califon; Steven E. Diamond, Springfield, both of N.J.

[73] Assignee: Allied Corporation, Morris Township, Morris County, N.J.

[21] Appl. No.: 863,750

[22] Filed: May 16, 1986

[51] Int. Cl.[4] .................. C12Q 1/68; C12P 19/34; G01N 33/566; C07H 19/06

[52] U.S. Cl. .................................. 435/6; 435/91; 435/810; 436/501; 935/77; 935/78; 536/26; 536/27; 536/28

[58] Field of Search .................. 435/6, 91, 810, 15, 435/21; 436/501; 935/77, 78; 536/26, 27, 28

[56] References Cited

U.S. PATENT DOCUMENTS 4,683,195 7/1987 Mullis et al. .................. 435/6
4,683,202 7/1987 Mullis .................. 435/91

FOREIGN PATENT DOCUMENTS 0063879 3/1982 .
123513 4/1984 European Pat. Off. .
WO84/02702-
21 7/1984 PCT Int'l Appl. .

OTHER PUBLICATIONS

Sanger, F. et al., Jour. Mol. Biol., 94:441–448, (1975).
Sanger, F., et al., Proc. Natl. Acad. Sci. USA, 74, No. 12:5463–5467, (1977).
Zimmern, D. et al., Proc. Natl. Acad. Sci., U.S.A., 75 No. 9:4257–4261, (1978).
R. K. Saiki et al., Enzymatic Amplification of B–Globin Genomic Sequences and Restriction Site Analysis for Diagnosis of Sickle Cell Anemia, Science, vol. 230, pp. 1350–1354, (1985).

Primary Examiner—Robert J. Warden
Assistant Examiner—Jack Spiegel
Attorney, Agent, or Firm—Alan M. Doernberg

[57] ABSTRACT

A probe polynucleotide binds to a target nucleotide sequence in the nucleic acid of a biological sample, and then is enzymatically extended in the 3'-direction with a mixture of nucleoside triphosphates including at least one nucleoside triphosphate that has been detectably labeled. After separating extended hybrid from unreacted nucleoside triphosphates, detectably-modified nucleotides which have been incorporated are determined. In some forms, the 3'-terminal nucleotide of the probe polynucleotide is selected to form a matched pair with some sample strands, but a mismatched pair with other sample strands. In such cases, if the primer dependent enzyme used for extension is one lacking 3'-exonuclease activity, then only those hybrids forming such a matched pair will be extended and subsequently determined.

24 Claims, 4 Drawing Sheets

```
         TBR
      ⌒⎴⎴⎴⎴⎴⎴⎴⎴⎴
     -dA-dT-dA-dG-dC-dA
     -rU-rA-rU-rC-rG-rU-rC-rC-rU-rA-rC-
      ⎵⎵⎵⎵⎵⎵⎵⎵⎵⌣
         TNS$_R$
```

METHOD AND KIT FOR POLYNUCLEOTIDE ASSAY INCLUDING PRIMER-DEPENDANT DNA POLYMERASE

BACKGROUND OF THE INVENTION

The present invention relates to assay methods and kits for detecting nucleotide sequences in the nucleic acid (DNA or RNA) of a biological sample.

Nucleic acid assays based upon the specificity of hybridization have been described, e.g., in U.S. Pat. Nos. 4,358,535 to Falkow, et al (1982) and 4,486,539 to Ranki, et al (1984) and in PCT Application WO 84/02721 of Kohne (1984). Nucleic acid assays also providing specificity at restriction sites have been described, e.g., in U.S. Pat. No. 4,395,486 to Wilson, et al (1983) and in B.J. Conner, et al, Proc. Nat. Acad. Sci U.S.A., vol. 80, pp. 278-282 (1983). There is a continuing need for improvement in such assays, particularly with regard to specificity, ease of use, reduced assay time, increased sensitivity and reduction in background signal. A particular need exists for assays capable of clearly distinguishing closely related sequences such as the highly conserved ribosomal RNA (rRNA) strands present in high copy number in related organisms (e.g., the rRNA strands of E. coli. and of Salmonella typhimurium).

EP-A-123,513 of Mundy (Amersham International) (1984) describes a method of detecting a single nucleotide mutation. A target strand (typically immobilied) is hybridized with a labeled probe to form a hybrid double-stranded region up to the nucleotide adjacent to the site of the suspected mutation. Probe extension is then conducted in the presence of a single modified nucleotide precursor (e.g., a thionucleoside triphosphate) that will extend the probe by one nucleotide if one base is at the suspected site, but not at all if any other base is at the suspected site. The duplex is then subjected to digestion conditions that will digest probe that has not been extended, but that will not digest probe which has been extended by one modified nucleotide. Label (elsewhere on the probe) is then detected if still in a duplex (i.e., if not digested).

BRIEF DESCRIPTION OF THE INVENTION

The present invention is based upon the selective incorporation of detectably labeled nucleotides into an elongation segment formed on a sample polynucleotide containing a target nucleotide sequence as template and as an extension of a probe polynucleotide (which need not be labeled, but may contain a site for specific immobilization) as primer.

Thus, the present invention provides a method for the determination of a target nucleotide sequence in the nucleic acid of a biological which comprises the steps:

(a) contacting the sample with a probe polynucleotide of a sufficient length under conditions sufficient for the probe polynucleotide to bind to the target nucleotide sequence and form a hybrid having a double-stranded portion including the 3' end of the probe polynucleotide, with the sample nucleic acid strand extending in a 3' to 5' direction beyond the 3' end of the probe polynucleotide;

(b) extending the probe polynucleotide strand of the hybrid beyond its 3' end in the 5' to 3' direction on the sample nucleic acid strand by incorporating nucleoside triphosphates from solution, a plurality of the nucleotides incorporated into the extended probe strand being detectably-modified nucleotides; and (c) detecting detectably-modified nucleotides which have been incorporated into probe polynucleotide strand as a measure of target nucleotide sequence in the biological sample.

The present invention also provides a kit for the determination of a target nucleotide sequence in the nucleic acid of a biological sample comprising:

(a) a probe polynucleotide complementary to the target nucleotide sequence, (b) a mixture of nucleoside triphosphates and enzyme sufficient for the extension of the probe polynucleotide by enzymatic incorporation of a plurality of nucleoside triphosphates to form an extended probe polynucleotide strand having a first plurality of nucleotides beyond the probe polynucleotide in a 5' to 3' direction, at least some of the nucleoside triphosphates being modified such that the first plurality of nucleotides contain a second plurality of modified nucleotides which are detectable.

The present invention also provides a probe polynucleotide having a sequence at its 3' end substantially complementary to the target nucleotide sequence to be detected, all but one of the nucleotides of the probe polynucleotide being deoxyribonucleotides and the 3'-terminal nucleotide of the probe polynucleotide being a ribonucleotide.

DETAILED DESCRIPTION OF THE INVENTION

The method and kit of the present invention are useful in the detection of target nucleotide sequence in sample nucleic acids (DNA or RNA) which are either recovered directly from a sample to be analyzed, or after culturing, replication or other treatments. Sequences may be detected generally or, as described below, individual nucleotides located at selected sites in the target nucleotide sequence can be detected.

In practice, primer directed elongation is easily effected on crude samples of double or single stranded nucleic acids. DNA or RNA is isolated following a cell lysis step (SDS, osmotic shock, lyzozyme, guanidinium chloride, etc.) using either a reverse phase, or hydroxy appatite type column. DNA or RNA so obtained is heated in the presence of the primer and in the presence of buffer salts. Following cooling the enzyme and nucleotides are added and polymerization is allowed to proceed as described below.

Figure 4A:
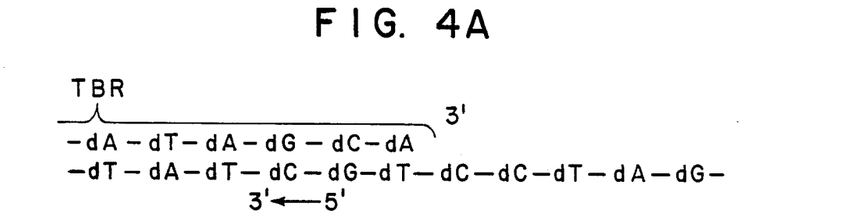
Figure 4B:
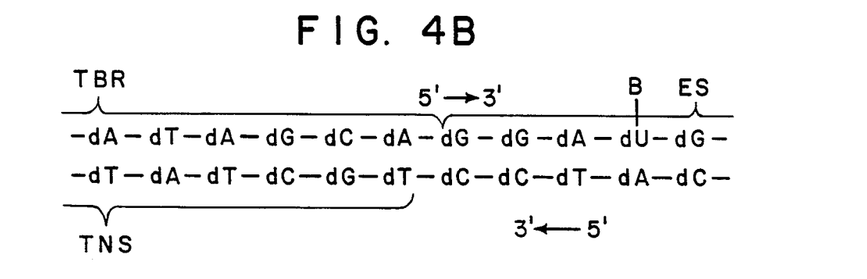
Figure 4C:
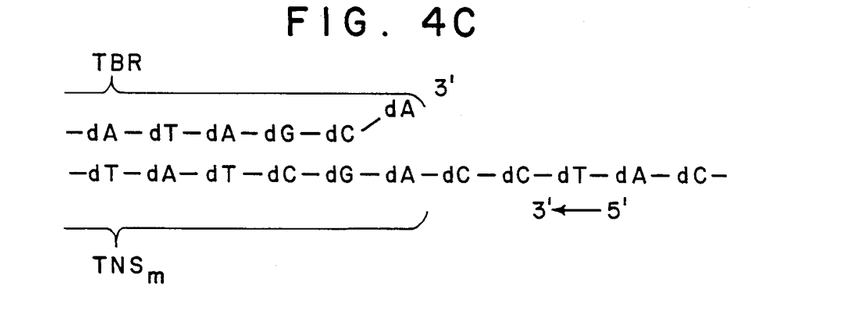
Figure 4D:
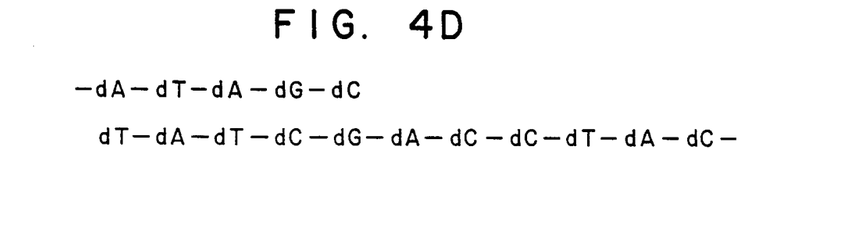

As in the method of EPA No. 123,513, the method begins with forming a hybrid between a probe polynucleotide or probe and the sample polynucleotide in single-stranded form. Probes of relatively short length (e.g., 10–100 nucleotides) are preferred in that they can be chemically synthesized. The probe can be DNA or RNA or, as described below, a continguous DNA-RNA polynucleotide (e.g, a ribonucleotide terminated DNA probe). The probe should form a hybrid with the target nucleotide sequence including the 3' end of the probe, and preferably including the 3' terminal nucleotide of the probe polynucleotide. When it is desired to detect to the base at a particular position in a sample polynucleotide, it is generally preferred to design the probe to form a duplex which includes such position at one end (paired to the 3'-terminal nucleotide) of the probe, as discussed below and as illustrated in FIGS. 4A and 4C. For the subsequent primer-extension stage, the sample nucleic acid strand (DNA or RNA) should extend in a 3' to 5' direction beyond such duplex, preferably for at least 100 further nucleotides. The contacting (hybrid forming) step can be performed under normal conditions of temperature, salt concentration and molar excess of probe for such reactions, depending in part on the length of the probe for optimal temperature and salt concentration to achieve optimal hybridization rates. Rate enhancers such as poly(ethylene glycol) can be used in this step as is conventional when using labeled probes in prior art processes.

The probe that has formed such a duplex is then subjected to enzymatic primer extension with enzyme such as Primer-dependant DNA Polymerases and Viral Reverse Transcriptases, including AMV Reverse Transcriptase, various eukaryotic primer-dependent DNA Polymerases and DNA Polymerase I from E. coli (Klenow fragment). Such enzymes have the effect of incorporating nucleoside triphosphates into an extension of the probe strand from the duplex on the sample nucleic acid strand, either selectively for duplexes that contain perfectly matched pairing at the 3' end of the probe, or non-selectively whether or not such 3' probe end is perfectly matched). Other factors in selecting the extension enzyme include: (1) whether the sample nucleic acid strand is DNA or RNA (e.g., only reverse transcriptases will effectively incorporate deoxynucleoside triphosphates into an extension product on an RNA template), and (2) ability to incorporate particular modified nucleoside triphosphates (biotin-dUTP, for example, is incorporate easily by Klenow, but not easily by AMV Reverse Transcriptase).

Unlike the use of primer extension in the elucidation of gene structure (see T. Maniatis, et al, Molecular Cloning: A Laboratory Manual, Chapter 7, pp. 211-246 (Cold Spring Harbor Press 1982)), the sequence of the extension portion formed is not of interest in the present invention. It is rather important that modified nucleotides can be incorporated into this elongation of the probe strand (for subsequent isotopic or non-isotopic detection): (1) if, and only if, probe has hybridized to sample and, (2) (in some cases) if and only if, the resulting duplex has a perfectly matched base pair at its end containing the 3'-terminal end of the probe.

As indicated in the description of the Figures below, some enzymes (e.g., AMV Reverse Transcriptase and eukaryotic primer-dependent DNA Polymerases) have no error-correcting activity, and therefore will primer-extend only probes which are bound in duplexes containing a perfect match at the 3' end of the probe. Other enzymes, such as Klenow, have an error-correcting activity, and therefore do not show this selectivity (although modifications of enzymes such as Klenow are now available, from Pharmacia, from which such activity is absent).

During the elongation step, all of the nucleotide precursors (i.e., nucleoside triphosphates) needed for elongation should be present, with at least one of such precursors in detectably-modified form: e.g., (1) dATP, dCTP, dGTP and biotin-dUTP or (2) $^{32}$P-dATP, dCTP, dGTP and dTTP. When $^{32}$P label is used, it should be in the alpha phosphate that will be incorporated into the elongation segment. Other radionuclides such as $^3$H, $^{125}$I or $^{14}$C can also be used in a modified nucleoside triphosphate. Other forms of modified bases besides biotinylated bases can be used, including halogenated and metallated deoxyribonucleoside triphosphates. It is preferred that nucleotides be ones that, when incorporated, permit the longest possible elongation segment to be formed; it is not, however, necessary that the elongation segment be suitable as a template for further replication. Temperature, salt concentrations and other conditions for the elongation reaction can be those commonly used for primer elongation with the respective enzyme.

It is preferred that the contacting (hybridizing) and extending steps be performed in solution for improved kinetics relative to solid phase reactions. There are embodiments, however, such as in situ hybridizations, where the sample polynucleotide is prepared for hybridization by the probe in cellular or tissue environments.

In some forms of the invention, the detection can also be performed in solution. It is preferred, however, to perform a separation after the elongation step that normally involves the elongated hybrid being immobilized (if it is not already on a solid phase). There are four general forms of such separation: (1) washing or separating unicorporated nucleoside triphosphates away from an already-immobilized elongated hybrid, (2) immobilizing the hybrid non-selectively with other larger polynucleotides and separating away the unincorporate nucleoside triphosphates, (3) immobilizing the hybrid selectively (e.g., by attaching to a binding segment on the probe) and separating away unincorporated nucleoside triphosphates together with sample polynucleotides that probe did not bind to, and (4) separating or inactivating modified nucleoside triphosphates without immobilizing elongated hybrids.

Form (2) is superior to conventional labeled probe assays even though essentially all sample polynucleotides are immobilized with the desired elongated hybrid. Little or no washing is required to remove non-specific label because the unincorporated nucleoside triphosphates are small and easily separated from the solid phase, while conventional labeled probes are large and notoriously difficult to wash completely from the solid phase. Note that in form (2) of the present method, it is not necessary to wash away excess probe that did not hybridize, since it does not contain label. The same factors apply in form (1), especially compared to in situ assays with labeled probes.

Form (3) offers still improved specificity and signal concentration in that a binding group (e.g., oligo-dC or pendant biotins) on the probe can be captured specifically by a solid phase material (e.g., oligo-dG-cellulose or avidin-agarose, respectively). In such case, elongated hybrids can be captured specifically and in high concentration on the solid phase, with the major other material captured (unhybridized probe) not causing non-specific signal.

Once the elongated hybrid is isolated from unincorporated nucleoside triphosphates, detection can proceed in a conventional fashion, either on the solid phase or otherwise. Thus elongated hybrids containing $^{32}$P can be detected by scintillation counting or autoradiography and elongated hybrids containing biotinylated nucleotides can be detected by contact with avidin-fluorescent molecule, steptavidin-enzyme conjugate or other similar labeled affinity reagent for the affinity moiety biotin. With biotinylated elongation segments on a solid phase, the ABC-type reagents (avidin plus biotin-enzyme conjugate) can be used to immobilized multiple enzyme molecules at each biotin along the elongation segment. In similar fashion, if the modified nucleotides incorporate into the elongation segment are halogenated nucleotides, then antibodies thereto conjugated with a fluorescent molecule or enzyme can be used.

It should be apparent that the binding system used in form (3) of the present method should be independant of the binding system used to attach detectable label to the modified nucleotides during the detection step (i.e., biotin/avidin cannot be used for both). Exemplary combinations for form (3) (selective immobilization of elongated hybrids) are tabulated below:

| | Probe Immobilization | Elongation Segment Contains |
|---|---|---|
| A | Biotinylated Nucleotides | Halogenated NTPs |
| B | Biotinlated Nucleotides | Isotopically Labelled NTPs |
| C | Sugar | Biotinylated NTPs |
| D | Mercurated Nucleotides | Biotinylated NTPs |
| E | Oligo-dC-tail | Biotinylated NTPs |

In cases A and B, the elongated hybrid can be recovered from reaction mixture with immobilized avidin or streptavidin. In cases C and D, immobilized lectin and immobilized thiols could be used for such recovery. In case E, oligo-dG-cellulose can be used. In case A, labeled antibody to halogenated nucleotides could be used for the contacting portion of the detection step. In cases C, D and E, labeled avidin or ABC reagents can be used for the contacting portion of the detecting step. Various other permutations of binding segment on the probe and affinity moiety on the modified nucleotide can also be used.

In addition to removing unicorporated modified nucleoside triphosphates from the elongated hybrid, form (3) of the method should permit removal of unpaired oligonucleotides that may have formed or elongation segments that may have occurred on sample templates not containing the probe (but rather a sample-originating primer).

The present invention is further illustrated by reference to the Figures.

Figure 1A:
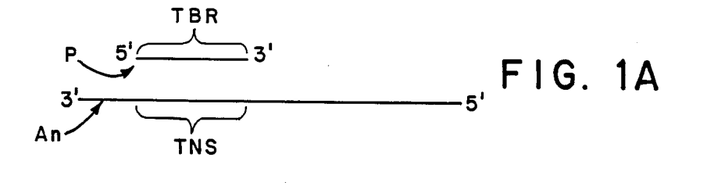
Figure 1B:
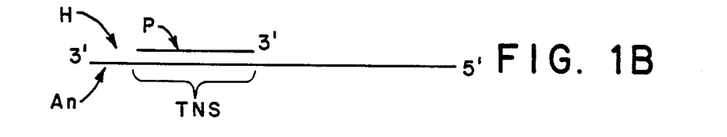

FIG. 1, comprising FIGS. 1A–1E, illustrates a first embodiment of the present invention. In FIG. 1A, an analyte strand An having the target nucleotide sequence TNS near its 3' end is shown. A probe polynucleotide P is produced as a reagent having a target binding region TBR complementary to sequence TNS. In this particular embodiment, probe polynucleotide P consists only of sequence TBR; in other embodiments, sequence upstream of TBR (closer to the 5' end than TBR) are also present in probe P. FIG. 1B shows the hybrid H which forms when probe P binds to analyte strand An by complementary base pairing of region TBR to region TNS. For the present, the case will be discussed wherein such complementary base pairing is either perfectly matched throughout TBR/TNS or has any mismatches remote from the 3' end of region TBR (which is also the 3' end of probe P).

By contacting the hybrid H shown in FIG. 1B with a DNA polymerase specific therefore, the strand of hybrid H which consisted of probe P will be elongated at its 3' end opposite analyte strand An which serves as a template for DNA replication. Probe P (and especially the 3' end of region TBR) serves as the primer for DNA replication. The DNA polymerase enzyme, primer and template are chosen together such that, if analyte strand TNS is RNA, then a reverse transcriptase DNA polymerase is used and a DNA probe strand P is used as primer. If analyte strand An is DNA, then either a reverse transcriptase, a primer dependant procaryotic DNA polymerase (e.g., E. coli DNA Polymerase I, Klenow (large fragment)) or a eukaryotic DNA polymerase may be used, with the probe P either being DNA or being RNA or being DNA with a 3' terminal ribonucleotide as described below in connection with FIG. 4H.

In this embodiment, the elongation is performed by incorporation of all four types of nucleoside triphosphates, at least one of which is detectably modified: e.g., dCTP, dGTP, dATP and bio-dUTP (the nucleotide mixture employed by Langer, et al, Proc. Nat. Acad. Sci., vol. 78, pp. 6633–6637 (1981)) (some corresponding unmodified nucleoside triphosphate, dTTP, can also be present). Accordingly, elongation segment ES of elongated hybrid EH shown in FIG. 1C will have a plurality of pendant biotin moieties, approximately one per four nucleotides.

Figure 1C:
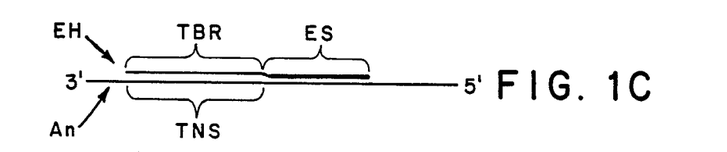

In similar fashion, elongation segments containing halogenated nucleotides (e.g., bromo-dU) or metallated nucleotides (e.g., mercurated deoxyuridine) can be formed by using the corresponding halogenated or metallated nucleoside triphosphates.

Figure 1D:
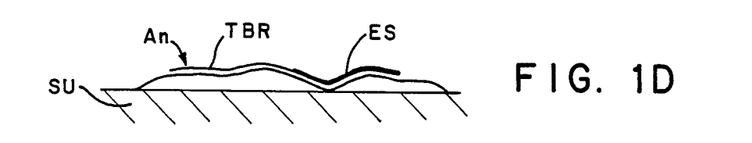

The elongated hybrid EH shown in FIG. 1C is now immobilized onto a support SU, as shown in FIG. 1D and washed to remove low molecular weight materials, and especially free bio-dUTP. It will be appreciated that such washing can be much less extensive than that required to remove unhybridized probes in the assays of Ward, et al (EPA No. 63,879) or commercial products produced by Enzo Biochem.

Figure 1E:
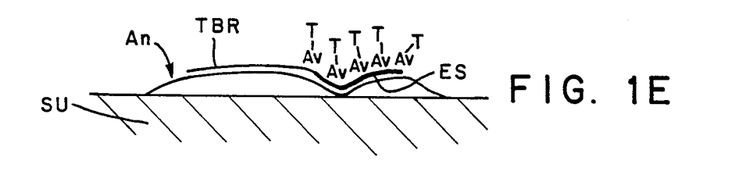

The immobilized elongated hybrid is now contacted with avidin-tag conjugated Av-T such as avidin-enzyme (e.g., avidin-horseradish peroxidase or avidin-alkaline phosphatase) or avidin-fluorescent tag (e.g., avidin-fluorescein), or by the corresponding streptavidin conjugates, or by soluble avidin and a biotin-tag conjugate (see the ABC detection procedure described in PCT publication WO 84/04970 of Ward, et al. (1984) and in the Hsu, et al articles referenced on page 6 of WO 84/04970). In all such cases, a complex will form on the support SU wherein several pendant biotins on elongation segment ES will each serve as an attachment site for one or more tags T. This is illustrated in FIG. 1E. After free avidin-tag conjugates (Av-T) or free ABC complex reagents are washed away, the tag may now be detected, directly (e.g., light measurement of fluorescent tags) or indirectly (e.g., by providing the chromogen-containing reagent for the enzymatic tag).

Figure 2A:
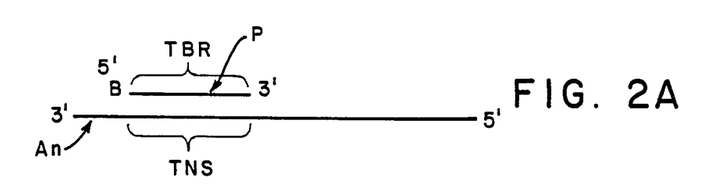
Figure 2B:
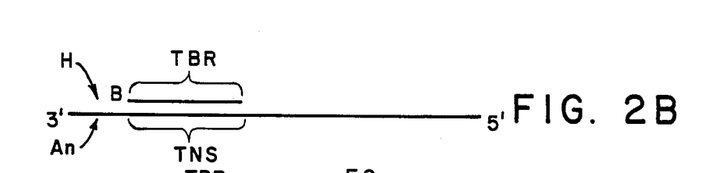
Figure 2C:
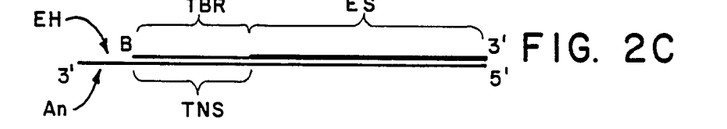

FIG. 2, consisting of FIGS. 2A–2D, illustrates a second embodiment of the present invention. In FIG. 2A, the analyte strand An containing the target nucleotide sequence TNS is shown, along with a probe polynucleotide P containing the sequence TBR complementary to sequence TNS and also containing at its 5' end a chemically attached biotin B (see Chollet, Andre and Kawashima, E.G., (1985) Nucleic Acids Research, 13, 1529–1541 for a representative technique for preparing such probes). When an excess of such probes P is added to a biological sample, hybrids such as hybrid H shown in FIG. 2B will form, with the perfectly matched duplex TBS/TNS formed. By then adding the appropriate DNA polymerase enzyme and mixture of nucleoside triphosphates, the 3' end of the region TBR can be elongated as shown in FIG. 2C toward, or to, the 5' end of the analyte strand An. If the incorporate nucleotides include a radioactively modified nucleoside triphosphate (e.g., using alpha-$^{32}$P-dATP) such tag will be incorporated at multiple sites within elongation segment ES.

Figure 2D:
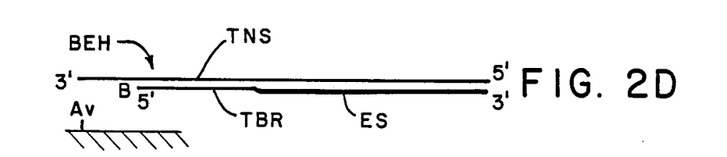

The reaction mixture containing elongated hybrid EH is now placed in contact with an immobilized affinity reagent for biotin (e.g., through an avidin-agarose column) so as to bind thereto by the biotin B at the 5' end of segment TBR, as shown in FIG. 2D. Washing the solid phase removes both free tagged nucleoside triphosphates and polynucleotides into which the tag may have been incorporated, but which do not contain the biotin B of probe P (see the above discussion of non-probe primed elongation reactions and of unprimed DNA polymerization reactions).

The solid support may now be assayed for the tag in a conventional manner, as described above, such as by autoradiography or by contact with labeled antibodies to halogenated nucleotides.

Figure 3A:
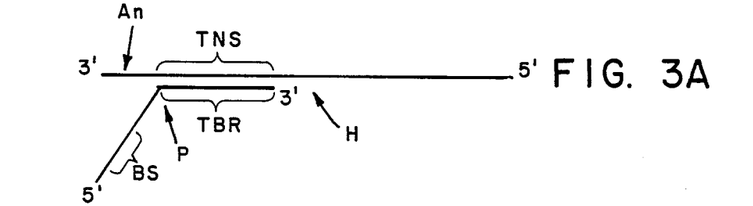
Figure 3B:
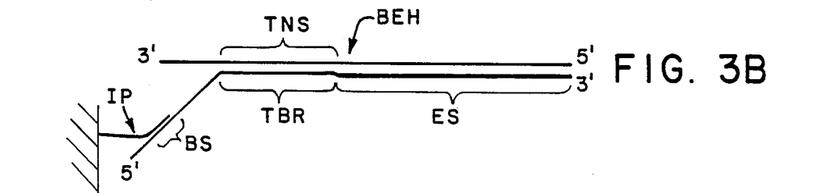

FIG. 3, consisting of FIGS. 3A and 3B, illustrates a third embodiment of the present invention by showing in FIG. 3A the probe/analyte hybrid H (analogous to FIGS. 1B and 2B) and by showing in FIG. 3B the bound elongated hybrid BEH (analogous to FIGS. 1D and 2D). As shown especially in FIG. 3A, the probe polynucleotide P contains region TBR at its 3' end complementary to the target nucleotide sequence TNS of the analyte strand An. Additionally, the probe P contains a binding segment BS nearer to its 5' end which can be homopolymeric (e.g., poly-dC, poly-rA, or poly-dG) or can be a defined sequence (e.g., of viral origin) not expected to be present in the sample nucleic acid. If biotin is not present in the modified nucleoside triphosphates used to form the elongation segment, then biotin can be present in or on the probe to serve the same purpose as the binding segment. When an excess of such probe P contacts a sample containing analyte strands An having the target nucleotide sequence TNS, hybrids H, as shown in FIG. 3A, form, including duplex region TBR/TNS.

By elongation with an appropriate DNA polymerase and mixture of nucleoside triphosphates (as described above), the strand of hybrid H having segment TBR is now elongated toward or to the 5' end of the analyte strand An. The reaction mixture is then contacted by an immobilized polynucleotide IP (or an immobilizable polynucleotide which is subsequently immobilized) having a sequence complementary to binding segment BS of probe P to cause the elongated hybrid to bind selectively thereto and form the bound elongated hybrid BEH shown in FIG. 3B. This bound elongated hybrid BEH (or the corresponding elongated hybrid bound to avidin if biotin is present in the probe P for this purpose) can be concentrated and separated from the remaining reaction mixture, which may contain various sources of non-specific signal such as adventitiously synthesized polynucleotides containing the modified nucleotide. Since the binding at segment BS is by complementary base pairing (unlike the avidin/biotin binding shown in FIG. 2D), the tagged nucleotides within segment ES can contain pendant biotins without causing inappropriate binding to the solid phase. The tags bound in the bound elongated hybrid BEH can now be directly or indirectly detected as described above in relation to FIG. 1D and to FIG. 2D.

In elongating the hybrids formed by the present contacting step (e.g., hybrids H of FIGS. 1B, 2B and 3A), it has thus far been assumed that complementary base pairing has been perfect, at least in the vicinity of the 3' end of region TBR. FIG. 4, comprising FIGS. 4A–4H, illustrates several situations involving terminal perfect matching or involving terminal mismatches that will affect the specificities of the enzymes used in the present invention.

In FIG. 4A a hybrid between the 3'-terminal TBR segment of the probe and the analyte strand is shown, with six matched base pairs of the TBR/TNS hybrid shown (compare FIGS. 1B, 2B and 3A). When such a hybrid is contacted by an appropriate mixture of nucleoside triphosphates (e.g., dATP, dCTP, dGTP and bio-dUTP) in the presence of an appropriate enzyme (e.g., E. coli DNA Polymerase I, large fragment (Klenow)), the probe strand can be elongated at its 3' end, with the probe serving as a DNA primer and the analyte strand serving as a DNA template. As shown in FIG. 4B, the elongated segment ES that forms will have dG opposite each template dC, dA opposite each template dT, dC opposite each template dG (none shown) and biotinylated deoxyuridine (B-dU) opposite each template dA. Under proper conditions, elongation will continue until the 5' end of the analyte strand is reached, and as many biotinylated deoxyuridines will be incorporated as the analyte strand has deoxyadenosines upstream of (closer to the 5' end than) the target nucleotide sequence TNS, typically 20–30% of the nucleotides of the analyte strand upstream of TNS.

Klenow in its native form (and most or all other primer-dependent DNA polymerases of procaryotic origin) also has endonuclease activity and is therefore not specific for target nucleotide sequences having a perfect match for the 3'-terminal nucleotide of the probe. Thus, in FIG. 4C, a hybrid is shown between the same probe shown in FIG. 4A and an analyte strand having target nucleotide sequence $TNS_m$ with dA instead of dT at the 5' end of the target region. The terminal dA of the probe now forms a dA/dA mismatch which, for steric reasons, is a poor site for primer-dependant DNA polymerase elongation. If the enzyme employed has substantially no endonuclease activity, under optimal conditions, significantly less incorporation will occur and sequence $TNS_m$ will not be detected. If an enzyme such as Klenow is used, however, the 3'-terminal dA of the probe can be removed by exonucleolytic phosphate hydrolysis (a reaction generally slower than elongation and thus not likely to occur in high frequency with the hybrid of FIG. 4A), leading to the hybrid structure shown in FIG. 4D wherein the dC residue previously one nucleotide removed from the 3' terminus is now the 3' terminal nucleotide of the probe strand. Elongation can now proceed, forming an elongated hybrid similar to that shown in FIG. 4B except that an incorporated dT will be present in the probe strand for the new hybrid where the probe dA nucleotide appears in FIG. 4B at the 3' end of segment TBR. Since the same number of biotinylated deoxyuridines will be incorporated into the new hybrid, analyte strands with segment $TNS_m$ will now be detected (along with analyte strands having segment TNS and analyte strands having modifications of segment TNS sufficient to form hybrids with probe P which are stable during any endonuclease activity and during elongation.

Figure 4E:
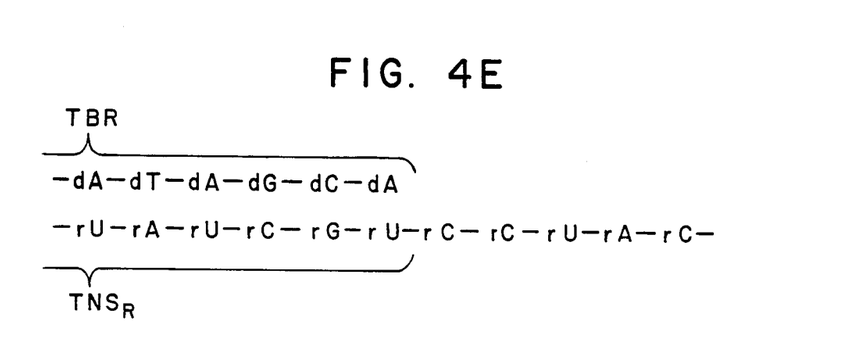
Figure 4F:
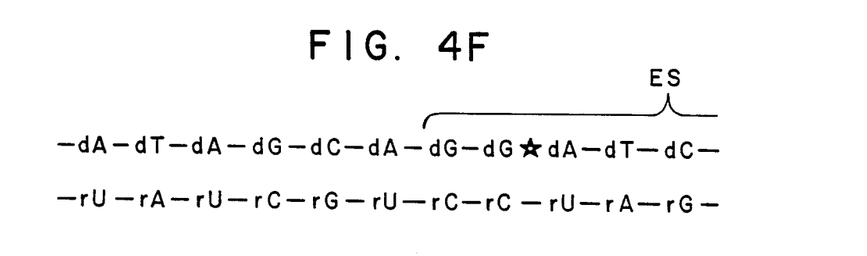
Figure 4G:
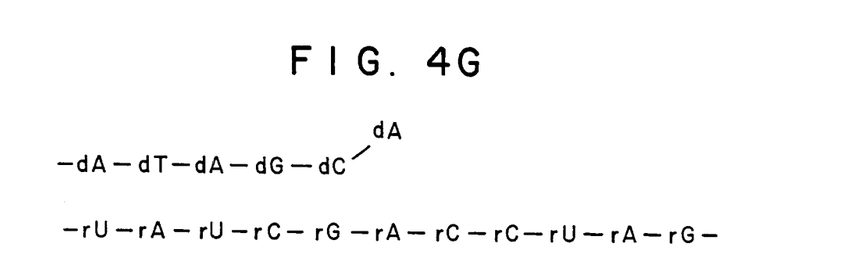

FIG. 4E illustrates the same probe with the same 3' terminal TBR region as shown in FIG. 4A, now hybridized to an RNA analyte strand with target nucleotide sequence $TNS_R$. By employing a reverse transcriptase enzyme, such hybrids can be recognized and the probe strand elongated as shown in FIG. 4F. Assuming that the nucleoside triphosphate mixture used is dGTP, dCTP, dTTP and alpha-$^{32}$P-dATP, the elongation segment ES will include a $^{32}$P-labeled dA nucleotide opposite each rC residue of the analyte strand, shown as a star in FIG. 4F between a dG residue and a dA residue (representing the phosphate linking such two deoxyribose sugar moieties, which had been the alpha phosphate of the alpha-$^{32}$P-dATP). If only labeled dATP is used, then as many as 20–30% of the incorporated nucleotides in elongation segment ES can have radioactive phosphorous in their phosphate linkage (the non-labeled phosphate linkages are shown as dashes in FIG. 4); if less than pure alpha-$^{32}$P-dATP is used, then only some of the incorporated dA nucleotides will have radioactive phosphorus. Since reverse transcriptase, in general, has no endonuclease activity, an RNA/DNA hybrid with a 3' terminal mismatch, such as is shown in FIG. 4G, will lead to suppressed elongation and incorporation of signal. Such suppression can be increased by selecting a probe sequence which perfectly matches the desired target nucleotide sequence at the 3' end of the probe, but contains more than one consecutive or non-consecutive mismatch at the 3' terminus when the probe binds to an expected sample nucleotide sequence which is desired not to be detected. This specificity is particularly useful in distinguishing rRNAs of closely related species (such as E. coli. and Salmonella typhimurium) or in distinguishing the mRNAs of closely related genes (such as genes for hemoglobin A and hemoglobin S), by suppressing elongation when the probe binds to the RNA sequence which is desired not to be detected. When one wishes to distinguish such closely related RNAs, one designs the probes to end at the nucleotide(s) which differ(s) (i.e., at the position on the analyte strand which is rU in FIG. 4E, but is rA in FIG. 4G). If one desires to detect the other RNA sequence (the one shown in FIG. 4G), one uses a modified probe having a terminal dT (i.e., terminating in the sequence dA-dT-dA-dG-dC-dT). Such modified probe will form a terminal mismatch with sequence TNS$_R$ shown in FIG. 4E, and therefore not be elongated thereon. If one desires instead to determine the sum of analyte strands with sequences as shown in FIG. 4E or as shown in FIG. 4G, one uses a probe with a 3' terminus at a point where the two are indistinguishable (e.g., the 3'-terminal sequence dA-dT-dA-dG-dC). It is of no great significance that, in this latter case, the first deoxynucleotide incorporated onto the RNA analyte strand shown in FIG. 4E will be dA, while the first deoxynucleotide incorporated onto the RNA analyte strand shown in FIG. 4G will be dT since so many dA nucleotides will be incorporated onto each RNA analyte strand that one $^{32}$P-labeled dA residue more or less per strand will not be significant.

The above discussion points out some of the distinctions between the present invention and the disclosure of European Patent Application No. 123,513 to Mundy (Amersham International 1984) in that the reference: (1) incorporates at most one nucleotide (instead of many) (2) provides only one nucleoside triphosphate (instead of four), and (3) is primarily specific as to the first unpaired nucleotide of the analyte strand in the hybrid (rather than providing specificity as to the analyte nucleotide opposite to the 3' terminal nucleotide of the probe).

Figure 4H:
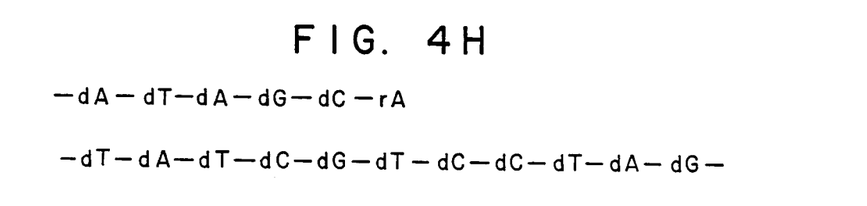

FIG. 4H shows a probe/analyte hybrid (of the type shown in FIGS. 1B, 2B and 3A) employing a DNA probe with a 3' terminal ribonucleotide. Such a probe (which is a particular feature of the present invention) is preferred over the probe shown in FIG. 4A when using a primer-dependent DNA polymerase of eukaryotic origin since such enzymes are likely to be more active in elongating primers having a 3' terminal ribonucleotide than in elongating primers having a 3' terminal deoxynucleotide. While a probe can also be used which is solely RNA, or which contains more than one ribonucleotide at the 3' terminus (e.g., has the 3' terminal sequence -dA-dT-rA-rG-rC-rA), the probe shown in FIG. 4H is expected to have superior stability relative to those probes in that it lacks any ribose to ribose phsophodiester linkage. Such ribose to ribose phosphodiester linkages serve as the most common site for reagent instability due, for example, to base-catalyzed or enzyme-catalyzed hydrolytic degradation.

It is relatively easy to prepare probe strands such as shown in FIG. 4H from the corresponding DNA polynucleotide having one less nucleotide (i.e., for the probe in FIG. 4H having the terminal sequence -dA-dT-dA-dG-dC), which has been prepared by cloning and restriction cleavage or by chemical synthesis. Reaction of such DNA polynucleotide with rATP in the presence of terminal deoxynucleotidyl transferase (TdT) and cofactors (see Methods of Enzymology, vol. 65, pp. 43–62) will lead to the incorporation of one or more rA nucleotides so as to produce the desired probe and also produce polynucleotides with 3' terminal sequences: -dA-dT-dA-dG-dC-rA-$(-rA)_n$ where n is 1 or more for each strand. Treatment by polynucleotide phosphorylase (PNP) (with high phosphate and no ribonucleoside diphosphates) or by base will cleave all of the ribose to ribose phosphodiester linkages and thus remove $(-rA)_n$ from the above-shown strands, leaving only the desired probe. It should be appreciated that the dC-rA linkage of the desired probe is a deoxyribose to ribose phosphodiester linkage, which is stable to base-catalyzed hydrolysis or PNP-catalyzed phosphorolysis.

EXAMPLES

In the following Examples, a series of oligonucleotides were used as probes (primers). They are designated PM-15, MM-15, PM23, MM-23, E-PM and Sal-PM and have the sequences shown in Table A:

TABLE A

PM-15 5'-TCCAGTCACGACGT-3'

MM-15 5'-TCCCAGTCACGACGA-3'

PM-23 5'-CCCCCCCCTCCCAGTCACGACGT-3'

MM-23 5'-CCCCCCCCTCCCAGTCACGACGC-3'

E-PM 5'-CACAACCTCCAAGTC-3'

Sal-PM 5' -CACAACCTCCAAGTA-3'

EXAMPLE 1

PRIMER DIRECTED ISOTOPIC DETECTION OF SINGLE STRANDED DNA'S.

DNA Preparation

DNA was purified from bacteriophage M13 particles by polyethylene glycol precipitation followed by extraction with a 25:24:1 (v:v:v) phenol, chloroform, isoamyl alcohol mixture as per established protocols.

Oligonucleotide Preparation

Oligonucleotides of length 15 to 23 bases were synthesized using standard phosphoramidite chemistry in an Applied Biosystems DNA synthesizer. The oligonucleotides are complementary to a portion of the mature M13 strand to the 3' side of the multiple cloning site region.

Hybridization protocol

M13 DNA ($1 \times 10^{-15}$ moles) was combined with 2.5 ug of such a 23-mer oligonucleotide, hereafter called PM23 DNA (approximately 330 pmoles) in a volume of 10 μl containing 0.01 M Tris HCl (pH 7.5) and 0.1M NaCl. PM23 has the sequence shown in Table A. This mixture was heated to 80° C. for 2 minutes and then cooled slowly to room temperature over a period of 10–20 minutes. To this was added an equal volume of a mixture containing deoxynucleoside triphosphates (excluding TTP) and biotinylated dUTP, $\alpha[^{32}P]$-dATP and E. coli DNA Polymerase I (Klenow large fragment and buffer components to the final concentrations shown in Table 1. The reaction was terminated following incubation of the reaction at 37° C. for 30 minutes by addition of urea and NaCl to final concentrations of 5 M and 0.5 M, respectively. An aliquot of each reaction was then passed over 30 mg columns of avidin-agarose held in a small Eppendorf pipette tip and washed with 5 ml of 5 M urea, 0.5 M NaCl. Counts bound to the column were quantitated by measurement of the Cerenkov radiation following placement of the individual columns into liquid scintillation vials. Table 2 shows the results of this experiment.

TABLE 1

Components for Primer directed isotopic Detection of analyte DNA by Klenow large fragment of DNA pol I

| (A) Hybrid Reaction volume (10 ul) | |
|---|---|
| Primer DNA | $3.30 \times 10^{-10}$ moles |
| Analyte DNA | $0-8 \times 10^{-15}$ moles |
| NaCl | 0.1 M |
| Tris HCl | 0.01 M |
| (B) Assay Reagent (10 ul) | |
| Tris HCl | 0.01 M |
| MgCl$_2$ | 0.02 M |
| Dithiothreitol | 0.02 M |
| dATP | 0.025 mM |
| $\alpha$ [$^{32}$P]dATP (3000 Ci/mmole) | 0.01 uCi |
| dGTP | 0.025 mM |
| dCTP | 0.025 mM |
| BiodUTP | 0.005 mM |

Klenow large fragment 1000 u/ml

TABLE 2

Measurement of Analyte DNA by Primer directed co-incorporation of Bio dUTP and $\alpha$ [$^{32}$P] dATP

| +DNA (1 fmol) +Primer (3.3 pmol) | −DNA +Primer | +DNA (10 fmol) −Primer |
|---|---|---|
| CPM retained | | |
| 9622 | 76 | 118.4 |
| Percent of cpm in column (%) | | |
| 6.5 | 0.05 | 0.08 |

EXAMPLE 2

The time course of co-incorporation of bio-dUTP and $\alpha[^{32}P]$ dATP were measured as a function of the presence or absence of primer and 0.1 fmol of homologous M13 DNA in the presence of 10 ng non-homologous denatured calf thymus DNA (final DNA concentration of approximately 1 ug/ml). The reactions were conducted exactly as in Example 1 and incorporation measured by termination of the reaction with urea/NaCl followed by passage of the sample over avidin-agarose columns followed by Cerenkov counting. These results are shown in Table 3.

TABLE 3

| | % Total Radioactivity Bound | |
|---|---|---|
| Time Min. | +Primer | −Primer |
| 0 | 0 | 0.001 |
| 0.5 | 0.03 | 0.002 |
| 1.0 | 0.054 | NM |
| 3.0 | 0.059 | 0.005 |
| 5.0 | 0.055 | 0.006 |
| 10.0 | 0.062 | 0.005 |

EXAMPLE 3

BASE SPECIFIC DETECTION OF ANALYTE DNA SEQUENCES

The presence of base changes in an analyte DNA were mimicked by preparation of 23 mer DNA primers of identical sequence except for the presence of a 3' terminal G in one case and a 3' terminal A in the other. They are designated mismatch (MM) or perfect match (PM), respectively, since a thymidine resides in the M13 analyte DNA strand at the position opposite the 3' terminal nucleotide of the primer. Since DNA polymerase I Klenow fragment possesses 3'→5' exonucleolytic activity which processes out mismatched bases, avian mycloblestosis reverse transcriptase (AMV-RT) was used for this assay.

The conditions for the hybridization and elongation reaction are shown in Table 4:

TABLE 4

Components for base specific detection of analyte DNA by AMV-RT

| (A) Hybrid Reaction (vol = 10 ul) | |
|---|---|
| Primer DNA | (300 pmoles) |
| Analyte DNA | $10^{-15}$ moles |
| Tris HCl (7.5) | 25 mM |
| KCl | 5 mM |
| (B) Assay Reagent (10 ul) | |
| Tris HCl | 10 mM |
| MgCl$_2$ | 5 mM |
| Dithiothreitol | 1 mM |
| dATP | 0.02 mM |
| dGTP | 0.05 mM |
| dCTP | 0.05 mM |
| TTP | 0.05 mM |
| $\alpha$ [$^{32}$P] dATP | 0.01 mCi |
| AMV-RT | 1500 u/ml |

Following incubation of the reaction for 30 minutes at 37° C., aliquots were placed on Gene Screen (TM) paper (from DuPont/New England Nuclear) and, washed extensively with 0.2 M NaCl. The amount of incorporation was quantitated by cutting and counting of the spots containing bound DNA. The time course of isotopic incorporation directed by PM and MM primers in the presence of and absence of 1 fmol of DNA is shown in Table 5.

TABLE 5

| | % Total Radioactivity Bound | | | |
|---|---|---|---|---|
| Time (Min) | −DNA PM | +DNA — | +DNA MM | +DNA PM |
| 0.5 | 0.003 | 0.002 | 0.001 | 0.02 |
| 1.0 | 0.002 | 0.002 | 0.002 | 0.06 |
| 3.0 | 0.001 | 0.004 | 0.003 | 0.07 |
| 5.0 | 0.003 | 0.001 | 0.002 | 0.08 |

TABLE 5-continued

| Time (Min) | % Total Radioactivity Bound | | | |
|---|---|---|---|---|
| | −DNA PM | +DNA — | +DNA MM | +DNA PM |
| 10.0 | 0.001 | 0.002 | 0.003 | 0.08 |

EXAMPLE 4

DISCRIMINATION OF E. COLI AND S. TYPHIMURIUM 16S RIBOSOMAL RNAS AT THE POSITION OF A SINGLE BASE MISMATCH

Preparation of Ribosomal RNAs

E. coli ribosomal RNAs were purchased from Boehringer Mannheim and used without further purification. High molecular weight RNAs of S. typhimurium were prepared from strain TA1537 of S. typhimurium. Following growth of bacteria, cells were precipitated, digested with lysozyme and the cells lysed by treatment with 1.0% Sarcosyl and 0.4 M NaCl. The reaction was extracted twice with phenol, chloroform, isoamyl alcohol (25:24:1) and the nucleic acids precipitated with 2.5 volumes of absolute ethanol at −20° C. The pellet obtained by centrifugation was redissolved in Buffer containing 5 mM CaCl$_2$, 0.1 M NaCl, 0.05M Tris HCl(pH 8.0) and 50 ug/ml. RNAse free DNAse 1.

Following incubation for 60 minutes at 37° C., the mixture was extracted and precipitated as above. Following centrifugation, the RNA pellet was redissolved in water to a concentration of 25 A$_{260}$/ml and the high molecular weight RNAs precipitated following addition of 0.2 volumes of 10 M LiCl for a period of 30–48 hours at 0° C. RNA so obtained was reprecipitated twice from 0.4 M NaCl in 75% ethanol to remove the residual LiCl, the pellets washed with 75% ethanol and the RNA redissolved in water for use. It was of interest to assess the single base specificity of the assay by choosing sequences which differs in only one position in the two rRNAs. To accomplish this, the primary structure of both organisms' small subunit ribosomal RNAs was studied by Sanger dideoxy sequence analysis. Sequence information covering approximately 300 bases in various regions of each 16S ribosomal RNA was obtained and compared for the two organisms. Using this approach, it was possible to rapidly pinpoint single base changes within identical blocks of RNA sequence. Using this information, two correspond regions of the E. coli and S. typhimurium 16S rRNA's were chosen for target sequences. These sequences, identical except for a single base difference (G→U), corresponding to position 823 of the E. coli 16S rRNA. Primers were constructed chemically (each 15 nucleotides in length see Table A) using phosphoramidite chemistry and subsequently tested for their ability to support AMV-RT-directed polymerization on the cognate and noncognate rRNA templates. As assayed by polyacrylamide gel electrophoresis, efficient incorporation of $^{32}$P-dATP into high molecular weight nucleic acid, occured only when the perfect match primer was annealed to the corresponding template. Incorporation was much reduced when the E. coli primer (E-PM in Table A) was hybridized to the S. typhimurim rRNA or when the S. typhimurium primer (Sal-PM) was annealed to the E. coli rRNA. The results were that, either with E-PM primer (probe) and its perfectly-matched RNA or with Sal-PM primer (probe) and its perfectly matched RNA, a dense spot on the autoradiograph was observed. With E-PM probe hybridizing to Salmonella RNA, the spot could not be seen. With Sal-PM probe hybridizing to E. coli RNA, only a light spot was observed. The 3' terminal nucleotide of each primer was mismatched in these hybrids that did not yield a dark spot.

EXAMPLE 5

PRIMER DIRECTED NON-ISOTOPIC DETECTION OF SINGLE STRANDED DNA

Reactions containing DNA (0–8 fmoles) and primer were conducted as in Example 1. Following reaction with Klenow and biotin-dUTP (cf Table 1) reactions were filtered onto Gene Screen ™ membranes held in a Lucite ™ dot blot apparatus. The spots were rinsed with 1 ml of 0.1% SDS in 1×standard sodium chloride sodium citrate solution (1×SSC). The filter was removed from the dot blot apparatus and incubated in a solution of 3% bovine serum albumin (BSA) for 45 minutes at 42° C. The filter was then incubated in 5 ml of a 1/2000 dilution of horse radish peroxidase-avidin (final enzyme conjugate concentration 2.5 ug/ml) in 0.05 M Tris HCl (pH 7.6) and 0.5% BSA for 15 minutes at 25° C. The filter was subsequently washed in four times in 20 ml 0.05 M tris HCl (7.6). The enzyme was visualized by incubation of the filter for 15 minutes at 25° C. in a solution containing 0.5 mg/ml diaminobenzidine, 0.03% hydrogen peroxide and 0.05 M Tris HCl (pH 7.6).

With or without SDS, the resultant spots on the Gene Screen membrane for various levels of analyte DNA were:

| fmol Analyte | Spot Density |
|---|---|
| 0 | Barely detectable |
| 2 | Light |
| 4 | Dark |
| 6 | Darker |
| 8 | Darkest |

We claim:

1. A method for the determination of a target nucleotide sequence in the nucleic acid of a biological sample which comprises the steps:
   (a) contacting a biological sample having a target nucleotide sequence unseparated from plural non-target polynucleotide sequences with a probe polynucleotide strand under conditions sufficient for the probe polynucleotide to bind only to the target nucleotide sequence to form a hybrid having a double-stranded portion including the 3' end of the probe polynucleotide, with the target nucleic acid sequence extending in a 3' to 5' direction beyond the 3' end nucleotide of the probe polynucleotide;
   (b) extending the probe polynucleotide strand of the hybrid beyond its 3' end in the 5' to 3' direction by using the target nucleic acid strand as a template strand and incorporating nucleoside triphosphates from solution, a plurality of the nucleotides incorporated into the extended probe strand being detectably-modified nucleotides; and
   (c) determining the amount of detectably-modified nucleotides which have been incorporated into probe polynucleotide strand as a measure of target nucleotide sequence in the biological sample.

2. The method of claim 1 wherein the contacting step (a) is performed in solution.

3. The method of claim 2 wherein the extending step (b) is performed in solution.

4. The method of claim 3 further comprising, after the extending step (b), separating from unincorporated nucleoside triphosphates polynucleotides including the extended probe polynucleotide strand.

5. The method of claim 4 wherein the separating step comprises immobilizing polynucleotides, including the hybrid of extended probe polynucleotide strand with target polynucleotide, onto a solid support and washing from the solid support unincorporated nucleoside triphosphates.

6. The method of claim 5 wherein the detecting step (c) is performed on the solid support.

7. The method of claim 6 wherein the detectably-modified nucleotides include an affinity moiety, and wherein the detecting step (c) comprises:
 (c1) contacting the solid support with a conjugate of a label and an affinity reagent of the affinity moiety, and
 (c2) detecting label adhering to the solid support.

8. The method of claim 5 wherein the probe polynucleotide contains an affinity moiety, and wherein the solid support contains an affinity reagent for the affinity moiety to specifically immobilize polynucleotides which contain the probe polynucleotide.

9. The method of claim 1 wherein the non-target nucleotide sequences are capable of binding to the probe polynucleotide during the contacting step (a) to form a mismatched hybrid including a mismatched base pair at the 3'-terminal nucleotide of the probe polynucleotide, and wherein mismatched hybrids are not extended during the extending step (b).

10. The method of claim 9 wherein the extending step (b) is performed with a primer-dependent DNA polymerase having substantially no 3' exonuclease activity.

11. The method of claim 10 wherein the target nucleotide sequence is RNA and wherein the primer-dependant DNA polymerase is a reverse transcriptase.

12. The method of claim 10 wherein the primer-dependent DNA polymerase is a reverse transcriptase.

13. The method of claim 10 wherein the target nucleotide sequence is DNA.

14. The method of claim 13 wherein the primer-dependent DNA polymerase is of eukaryotic origin.

15. The method of claim 1 wherein the biological sample comprises intact cells or tissue, and wherein hybrids form in situ during the contacting step (a).

16. The method of claim 15 wherein the having target nucleotide sequence is single-stranded RNA.

17. The method of claim 15 wherein the having target nucleotide sequence is double-stranded sample DNA and wherein, prior to or during the contacting step (a), the double-stranded sample DNA is denatured.

18. The method of claim 17 wherein the double-stranded sample DNA is heat denatured in the presence of probe polynucleotide.

19. The method of claim 1 wherein the having target nucleotide sequence is double-stranded sample DNA and wherein, prior to or during the contacting step (a), the double-stranded sample DNA is denatured.

20. The method of claim 19 wherein the double-stranded sample DNA is heat denatured in the presence of probe polynucleotide.

21. A kit for the determination of a target nucleotide sequence in the nucleic acid of a biological sample comprising:
 (a) a probe polynucleotide comprising a primer sequence substantially complementary to target and non-target nucleotide sequences in a biological sample, wherein said target nucleotide sequence contains a nucleotide complementary to the 3'-terminal nucleotide of said probe to form a template for primer-dependent nucleic acid polymerase and wherein said non-target nucleotide sequences contain nucleotides not complementary to said 3'-terminal nucleotide of said probe;
 (b) a plurality of nucleoside triphosphates, wherein at least one of said nucleoside triphosphates is modified to contain a detectable label; and
 (c) a primer-dependent nucleic acid polymerase which is substantially free of exonuclease activity, wherein said polymerase extends primers in a 5' to 3' direction when the 3'-terminal nucleotide of the primer is complementary to a nucleotide on a template polynucleotide sequence.

22. The kit of claim 21 wherein the primer-dependant nucleic acid polymerase is a reverse transcriptase.

23. The kit of claim 21 wherein the primer-dependant nucleic acid polymerase is a primer-dependant DNA polymerase of eukaryotic origin.

24. The kit of claim 21 wherein said modified nucleoside triphosphate is biotin-modified deoxyuridine triphosphate.

* * * * *